United States Patent
Voit et al.

(10) Patent No.: US 7,283,883 B2
(45) Date of Patent: Oct. 16, 2007

(54) METHOD AND DEVICE FOR OBTAINING ORTHOSIS MODELS

(75) Inventors: Jenny Voit, Rosenheim (DE); Dino Gallo, Bernau (DE)

(73) Assignee: Ortho Solutions OHG (DE)

( * ) Notice: Subject to any disclaimer, the term of this patent is extended or adjusted under 35 U.S.C. 154(b) by 246 days.

(21) Appl. No.: 10/802,315

(22) Filed: Mar. 17, 2004

(65) Prior Publication Data
US 2005/0209726 A1    Sep. 22, 2005

(51) Int. Cl.
*G06F 19/00* (2006.01)
*G06K 9/00* (2006.01)
*G06G 7/48* (2006.01)

(52) U.S. Cl. .......... 700/97; 700/117; 700/182; 382/128; 623/901; 703/6

(58) Field of Classification Search ........... 700/28–31, 700/56, 62, 83, 95, 97, 98, 117, 118, 163, 700/173, 180, 182, 197; 382/128; 623/66.1, 623/901; 702/167; 264/16; 715/964; 703/6; 707/102
See application file for complete search history.

(56) References Cited

U.S. PATENT DOCUMENTS 5,741,215 A * 4/1998 D'Urso .............. 600/407
5,850,836 A * 12/1998 Steiger et al. .............. 600/300
5,946,370 A * 8/1999 Adler et al. .................... 378/4
6,463,351 B1  10/2002 Clynch

FOREIGN PATENT DOCUMENTS

EP    1188421    3/2002
WO   WO 03/065931    8/2003

* cited by examiner

*Primary Examiner*—Leo Picard
*Assistant Examiner*—Sean Shechtman
(74) *Attorney, Agent, or Firm*—William H. Honaker; Dickinson Wright PLLC (57) ABSTRACT

The present invention provides a method and a device for producing an orthosis model for a patient. The method comprises the input of patients' data, the determination of a curvature type of the patient's spine to be treated from a predefined number of curvature types in dependence on the patient's data, and the selection of at least one orthosis model from a predefined number of models of orthoses in dependence on the specific curvature type. The device comprises a data input device being designed for inputting patients' data, a data base containing a number of curvature types and a number of orthoses models, a curvature determination device designed to determine a curvature type from the data base in dependence on the patients' data, and an orthosis model selection device designed to select at least one orthosis model from the data base in dependence on the determined curvature type.

20 Claims, 4 Drawing Sheets

METHOD AND DEVICE FOR OBTAINING ORTHOSIS MODELS

BACKGROUND OF THE INVENTION

The present invention relates to a method and a device for obtaining and producing orthoses models, especially trunk orthoses and braces, suited for the treatment of curvatures and deformations of the human spine as well as of scoliosis. In another aspect the invention concerns a method and device for obtaining orthoses or prosthesis models, especially prosthesis shafts for replacement of defective body parts of the patient.

Orthoses, i.e medical corsets or braces, are used for the treatment of the so-called scoliosis, i.e. a permanent lateral curvature of the body axis. The strive for correction by means of such braces is to avoid operations, if possible, a cosmetic improvement is to be achieved, and the well-being of the patient is to be reproduced eventually. For achieving a successful treatment it is necessary that the corresponding brace be worn practically all day long, which is, of course, an uncomfortable burden for the wearer in everyday life. The patient will therefore be willing to accept these restrictions only, if the wearing comfort is as high as possible, i.e. if the fitting accuracy is good.

For this reason, and also for reasons of costs, a high primary fitting accuracy is necessary, i.e. the brace or the orthosis must have a good fit without any elaborate finishing, and it must ensure the desired correction of the spine. So far, this has been achieved by a largely individual piece production: For this purpose, for example, plaster casts of the patient's back are made and sent to a manufacturer of orthoses along with comments from the diagnosing medical specialist and orthopedist, who will then produce the orthosis partially from existing modules and partially with individually prepared parts, with the orthosis requiring an additional elaborate finishing in the end.

For ensuring an effective and reproducible success as a result of the treatment it must be guaranteed, however, that a suitable brace or, respectively, a suitable model is produced. In case of the described piece production there is the great danger, that strongly varying final products are made due to the subjective individual evaluation of the same curvature patterns. Since, in this case, the diagnosis is made by a plurality of different parties (doctors, clinics), it is not guaranteed that the best possible brace is chosen in each case, namely always the same brace as above for cases with a comparable curvature. This is also based on the fact that the higher rated scoliosis in need of treatment is comparatively rare in orthopedic practice, with the result, that many parties are unable to gain a great deal of experience in diagnostics. Therefore, a standardized selection system would be desirable and necessary. Only such a system can allow the reproduction of the successful treatment, whereby the effectiveness of certain brace models is controlled, so as to prove and document the anticipated success of the treatment given certain curvature patterns.

On the other hand, the system for allocating the curvature pattern of the patient's spine to a suitable orthosis must not be too rigid in order to allow account for the individual situations of the different patients. Therefore, the system must be flexible and should allow an easy adoption to possibly new occurring problems, e.g. to a newly occurring curvature type.

Given the permanent increase of expenses in public health, the production process should thereby also incur as little cost as possible. This can hardly be achieved by the aforementioned individual production. Moreover, it is desired that the preparation of the brace can take place within a short time after the diagnosis was made, i.e. that the production is not too time-consuming. This issue, too, is not reliably ensured by the individual production.

Therefore, there is a need for a production method for orthoses or orthoses moulds and a device suited therefor, which can provide a solution to the aforementioned problems. This means that the production of the orthoses must be inexpensive and easy and as fast as possible, whereby the produced orthosis has to ensure the aimed correction by a high fitting accuracy.

SUMMARY OF THE INVENTION

According to an aspect of the invention a method for producing an orthosis model for a patient is provided. The method comprises the input of the patients data, the determination of a curvature type of the patients spine to be selected from a predefined number of curvature types in dependence and on the basis of patient's data, and the selection of at least one orthosis model from a predefined number of models of orthoses in dependence and on the basis of the specific curvature type.

The method according to the invention thus allows the determination of the abstract standardized curvature type from the data of the patient in a standardized way, i.e. for example from radiographs of the spine, the static dimensions of the body, the dynamic dimensions of the body, i.e. the ability to straighten up a deformed spine. This is, for instance, done on the basis of the radiographs, which show the number of the points of inflection. According to the detected curvature type a suitable, or possibly several suitable orthoses models can be selected. Since this is done on the basis of the abstract curvature type or pattern, false estimations due to purely individual patients' features are avoided.

It is preferred that the patients' data contain one or more elements from the group of radiographs, photos of the patient's back, static body dimensions, dynamic body dimensions and the age of the patient As a rule, combinations of the aforementioned elements are used, whereby individual elements are preferentially evaluated in view of different aspects. For example, the radiographs are a preferred element for determining the curvature of the spine. For selecting an appropriate orthosis, however, the body dimensions additionally have to be taken into account, namely both the purely static ones and the dynamic ones. "Dynamic" in this case refers to the ability to straighten up a deformity, which is, of course, a parameter necessary for the orthosis, indicating how strong the correction can be or should be at all. Ideally, of course, a spine as straight as possible should be achieved. Depending on the dynamic body dimensions or the age it may be necessary, however, to correct the spine only up to a certain degree.

It is preferred that at least two orthoses models are selected. Then, one orthosis model is selected from the at least two orthoses models. This takes place in dependence on the patient's data. If, for instance, two (or more) different orthoses models are suited and were determined for a specific type of curvature, a selection can be made between the two models on the basis of the patient's data so as to obtain the final orthosis model. It would, for instance, be conceivable that one model out of those two is suited for a rather slim person, while the other one is rather suited for a more corpulent person. Such a selection can then be made on the basis of the patients' data.

It is preferred that the patients' data are determined prior to the input. It is, of course, desirable that the determination of the input takes place in a directly preceding step.

It is preferred that the selected orthosis model is modified in accordance with the patient's data. Since an orthosis model is selected primarily in accordance with the (abstract) curvature type, adaptations to the wearer's need normally be made, for example, due to the body height, and possibly also due to other factors. Certain places on the patient's body can, for example, be sensitive to pain so that recesses have to be provided. The individual patients' data have to be used for such adaptations so as to allow the production of a best suitable orthosis.

It is preferred that the modified orthosis model be added to the predefined number of orthoses models. Due to the expansion of the data basis caused thereby a selection from a larger number of models can be made for future determinations. The determination of an appropriate model thus becomes more and more selective.

It is preferred that an orthosis mould is produced in accordance with the selected or modified orthosis model. The production should likewise be closely associated with the determination of an appropriate model so as to avoid errors.

It is preferred that the produced orthosis mould is refinished. It will partly be necessary that, despite of a preceding best possible accurate adaptation, an exact adaptation to the respective wearer of the orthosis is required. Such a possibility must therefore be provided.

It is preferred that the refinished orthosis mould is read in. The orthosis model according to the read-in orthosis mould is then added to the predefined, predetermined or at least predeterminable number of orthoses models. Thus, orthoses models which have undergone subsequent modifications compared to already predetermined models can be passed back into the cycle. Such a reading-in can, for instance, take place with a laser scanner or the like.

It is preferred that a new curvature type is determined from the patient's data. This type is added to the predefined number of curvature types. Once it is detected that the patient's data define a new type of curvature, i.e. for example a newly occurring type of deformation, this new type can thus be preserved for later determinations. This allows for a better determination of the curvature type for following patients.

According to another aspect of the invention a computer program product is provided. It comprises a program code for executing all steps of a method according to an above-described inventive method.

According to another aspect of the invention a computer program product is provided. It comprises a program code for executing all steps of a method according to an above-described inventive method, with the program code being stored on a computer-readable data carrier.

According to another aspect of the invention a computer program product is provided. It comprises a program code for executing all steps of a method according to an above-described inventive method, which is at least partially provided by a network such as the Internet.

According to another aspect of the invention a computer data signal is provided, which is contained in a carrier wave and comprises commands for causing a computer to execute all steps of a method according to an above-described inventive method.

According to another aspect of the invention a device for producing an orthosis model is provided. The device comprises a data input device designed to input patients' data, a data base containing a number of curvature types and a number of orthoses models, a curvature determination device designed to determine a curvature type in dependence on the patients' data, and an orthosis model selection device designed to select at least one orthosis model from the data base in dependence on the determined curvature type. Such a device according to the invention allows the inexpensive production of orthoses which are well adopted to the respective wearer in a standardized manner.

It is preferred that the data base comprises one-valued or many-valued allocations of curvature types to orthoses models, and that the orthosis model selection device is suited to select at least one orthosis model on the basis of these allocations. By means of allocations a very flexible selection can be made. As a rule, one or more orthoses models will be allocated to one curvature type, but it may preferentially also be vice versa.

It is preferred that the orthosis model selection device is suited to select at least two orthoses models, and that the orthosis model selection device is moreover designed to select one orthosis model from the at least two orthoses models in dependence on the patient's data. If several orthoses models are allocated to one curvature type, a selection from this plurality of models must be made on the basis of additional patient's data, which are not dependent on the kind of curvature.

It is preferred that the device comprises a means for obtaining the patients' data, with said means being designed such that the obtained patients' data are inputted into the data input device. Thus, the obtainment and the data input can be combined with each other.

It is preferred that the device comprises a data processing system, with said data processing system being designed such that the selected orthosis model is modified according to the patient's data. As described above, an adaptation may be required due to individual data of the patient (body circumference etc.).

It is preferred that the data processing system is designed such that the modified orthosis model is added to the predefined number of orthoses models in the data base. Thus, the data basis is expanded for future selections.

It is preferred that the data processing system is designed such that the one-valued or many-valued allocations of curvature types and orthoses models in the data base are modified or that new ones are generated. If it is detected that certain allocations are not suited for determining an orthosis model as appropriate as possible, a corresponding allocation can thus be modified. Also in the case of new curvature types and/or models a corresponding allocation may be added.

It is preferred that the device comprises a shaping device, with the shaping device being designed such that an orthosis mould is produced according to the selected or modified orthosis model. This allows a direct production of the orthosis in a short time period.

It is preferred that the device comprises a reading-in device for reading in an orthosis mould, with the reading-in device being designed such that an orthosis model is added to the number of orthoses models in the data base in accordance with the read-in orthosis mould. Possibly refinished orthoses models or models not stored so far can thus be added in an easy fashion.

It is preferred that the data processing system is designed to determine a new curvature type from the patients' data, and to add the new curvature type to the predefined number of curvature types in the data base. Thus, a newly detected curvature type may be added to the data base and is available for succeeding patients.

According to another aspect of the present invention there is provided a method for producing an orthosis or prosthesis model for a patient, comprising: inputting patient data and calculating at least one orthosis or prosthesis model for the patient on the basis of said patient data. On the basis of a huge amount of empirical data obtained from previous orthosis and prosthesis models in combination with respective patient data a calculation method can be derived to calculate orthosis and prosthesis models directly from patient data.

Preferably said step of calculating comprises interpolating between different orthosis or prosthesis models, the patient data of which are: known and accessible. Thereby the desired orthosis or prosthesis model, particularly orthosis shaft can be determined by interpolating between accessible model and patient data.

In a preferred embodiment said step of calculating comprises determining a curvature type of the patient's bone to be selected from a predefined number of curvature types on the basis of patient's data, and selecting at least one orthosis or prosthesis model from a predefined number of orthosis or prosthesis models on the basis of the determined curvature type.

According to a further aspect there is provided a device for producing an orthosis or prosthesis model, comprising a data input device designed for the input of the patient's data; a data base containing a number of orthoses or prosthesis models and a plurality of corresponding patient data; each orthoses or prosthesis model corresponding to a set of patient data, and an orthosis or prosthesis model calculation device designed to calculate at least one orthosis or prosthesis model from the data base in dependence and on the basis of the input patient data. Preferably said data base also contains a number of curvature types. In a preferred embodiment there is also provided an interpolating means for interpolating between orthosis or prosthesis models on the basis of patient data coming close to the input patient data.

In another preferred embodiment said calculation device comprises two determination components to determine a curvature type of the patient bone or spine and to determine an orthosis or prosthesis model oh the basis of said curvature type.

BRIEF DESCRIPTION OF DRAWINGS

Additional features and advantages of the invention are obvious from the following description, in connection with the drawing, wherein.

DETAILED DESCRIPTION OF DRAWINGS

It should be noted that the orthosis mould can, in the following, be understood in terms of a positive mould and a negative mould. The present invention is not restricted to one embodiment thereof. In the case of a negative mould merely another trivial production step is required, which shall not be described separately.

Not least due to the constantly increasing costs in public health is there a need for a standardized method for the production of orthoses or orthoses moulds, respectively, as is provided by the present invention.

For achieving a constant attendance quality it is desirable that the selection and production of a fitting orthosis for the respective patient takes place in a standardized manner. Thus, errors in the individual evaluations of different parties (doctors, clinics etc.) can be avoided, which are otherwise almost bound to happen.

By a method easy to apply and quickly leading to results, i.e. ready-to-wear orthoses, the attendance can be improved and the patients' satisfaction can be augmented. The patient merely has to appear for the obtainment of the data and the final adaptation or fitting, respectively. In view of the data obtainment merely a number of basic data have to be obtained, e.g. radiographs of the spine, static body dimensions as well as so-called dynamic antropometric data indicating the ability to straighten up the deformity of the spine. Moreover, certain data not directly associated with the spine may be important, e.g. the age of the patients.

The high primary fitting accuracy obtainable with the orthoses produced according to the present invention entails a smaller complexity during the subsequent adaptation on the patient and, thus, a greater acceptance by and greater satisfaction of the patient. The production of the orthosis within a short period of time avoids the occurrence of changes or even further deteriorations of the patient in the meantime resulting in the subsequent additional adaptation of the orthosis.

The inventive allocation of the patient's data to the required model ensures a secure attendance of a constant quality. Due to the invention the acquisition of expensive apparatus can largely be avoided or, respectively, limited to central areas.

One of the essential advantages of the method according to the invention resides in the capability of self-adaptation. The cycles as used entail the increasingly improving adaptation or, respectively, allocation of patients' data/curvature type/fitting orthosis. It is possible to subject each brace individually adapted to a patient to the data base, which renders the allocation in the method according to the invention more and more selective the more patients' data/braces are stored. If in the case of the allocation of the received patient's data to a brace it is found that the suitability of the available basic models is too insufficient, it may be required to design a completely new basic model. Such a basic model must then be abstracted from the patient's data for the newly detected curvature type. Said newly detected curvature type and orthoses models adjusted thereto are then added to the data base and are directly available to succeeding patients.

The storage of individual patients' data and the allocated adapted braces (on the basis of the existing basic models) according to the inventive method primarily serves to improve the allocation of newly obtained patients' data to existing basic models and the necessary fine adjustments. For this, it is moreover useful to add, if necessary, the characteristics of the treatment to the data. Thus, it can statistically be determined how effective the application of certain basic models is and how good the allocation patient/basic model is.

The self-adapting method according to the present invention is able to provide, along with an increasing number of treated patients and produced orthoses, respectively, an increasingly better and more reliable attendance. Since, on the one hand, information flow back into the cycle and do not get lost, while the evaluation is always performed centrally with a constant quality, both flexibility and reproducibility are guaranteed. Thus, errors caused by the inevitably individually colored evaluations made by many different parties, e.g. a plurality of different doctors who will inevitably make statistically fluctuant evaluations, are largely avoided. However, the feedback also allows the individual judgment by the possibly required subsequent adaptation of a brace to the patient. To this end, manually refinished orthoses can be entered into the data base, e.g. by reading them in with a laser scanner.

The data hereinafter called patients' data may be different data, e.g. radiographs of the spine, and photographs showing the curvature: of the back. Moreover, the data not directly associated with the spine may be included. These comprise, for example, special characteristics such as sensitive places onto which no pressure must be exerted by the orthosis, or the age of the patient,: an additional data which are of interest for determining an appropriate brace model.

According to the present invention the (abstract) curvature type is determined from a plurality of basic types in a first step by the evaluation of the patient's data. The individually adapted orthosis is then derived from this basic type or, respectively, from an allocated basic model of an orthosis, namely by scaling or modifying the basic model in correspondence with the patient's data. While the curvature type, i.e. for example the number of points of inflection and the directions of the curvature of a spine, constitutes an abstract value which is, in principle, independent of the body dimensions of the patient and his age, the individual data independent of the curvature must be taken into account for the patient-specific brace. Individual date are, for instance, the body dimensions (static) and also the dynamic antropometric data, i.e. the ability to straighten up the spine or the deformity thereof, respectively, as well as the age of the patient. While the abstract curvature type derived from the patient's data is employed for selecting one or more allocated basic models of the orthoses, the individual patient's data are included in the selection and adaptation of the best suited basic model up to the final orthosis. Thus, for example, three different orthoses models are selected according to one curvature type. By taking into account the patient's data, the most suitable model is then selected from those three, which is then again modified so as to be adapted to the wearer. Also data may be included, which are not directly associated with the spine. The patient could, for instance, have places on his body onto which no pressure must be exerted, since this could cause him pains. As a consequence, one orthosis model may now be selected out of several orthoses models suited for the type of curvature, with which no pressure need be exerted onto this place, or a corresponding recess may be provided during the modification thereof. The procedure as described simultaneously ensures a good reproducibility and a best possible adaptation to different patients.

Figure 1:
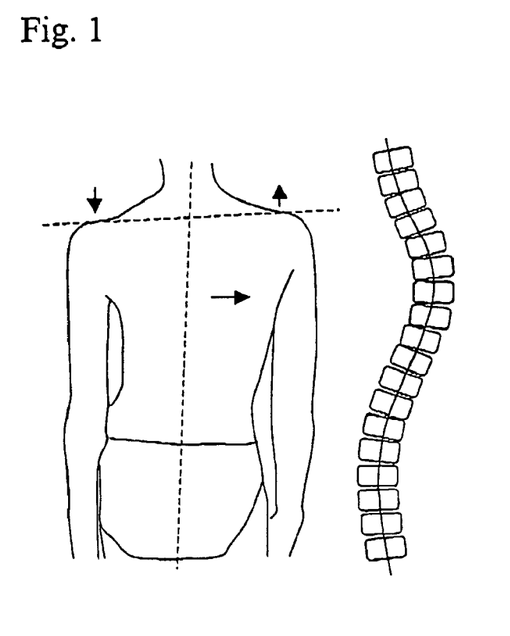
FIG. 1 shows a schematic view of a female patient's back showing a scoliosis example in the view to the back of a female patient, and the respective form of the spine.

FIG. 1 shows a possible form of scoliosis, with the respective spine shape being illustrated on the right-hand side. The curvature as shown herein has lead to an obliqueness of the shoulders. Compared with the right shoulder the left shoulder is clearly lower. The body is not symmetrical as can be seen from the ideal mean position indicated by a dashed line. As can be seen from the right-hand side of the figure, the spine is clearly curved.

Figure 2:
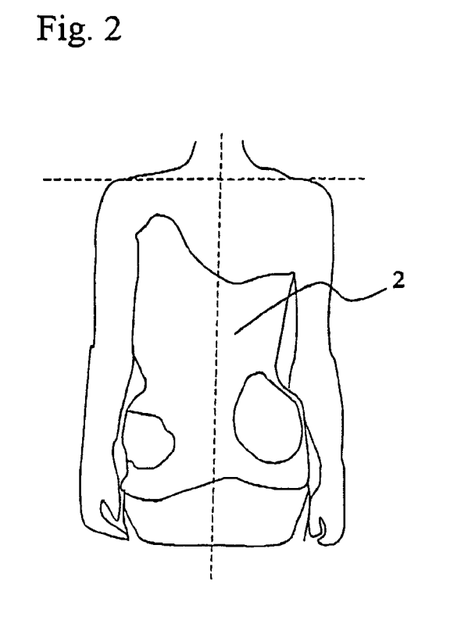
FIG. 2 shows a trunk orthosis worn by the female patient shown in FIG. 1.

FIG. 2 shows a trunk orthosis 2 adapted to the female patient shown in FIG. 1. It can already be recognized that, due to the effect of the brace, the body has become clearly more symmetrical compared to the dashed mean position shown in FIG. 1.

Figure 3:
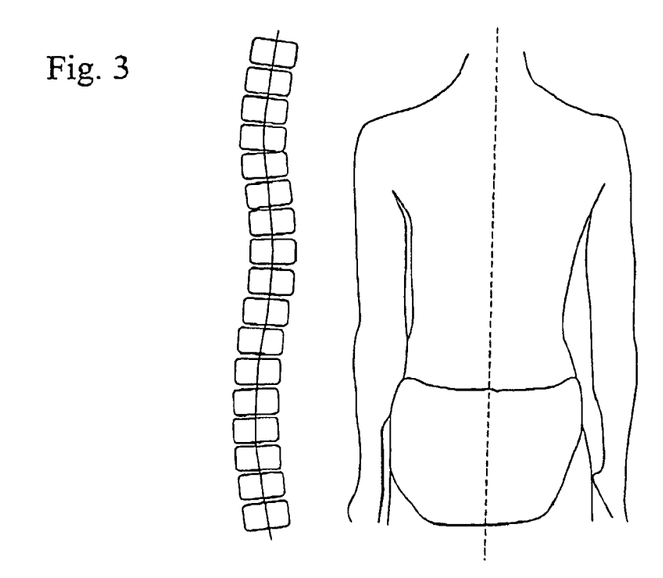
FIG. 3 shows a stadium desired after the treatment with an orthosis, and the respective form of the spine.

FIG. 3 finally shows a state of the female patient shown in FIG. 1, as it could look like after a treatment with an orthosis. The body has become clearly more symmetrical, the shoulders are positioned on approximately the same height, and the lateral spine curvature was reduced.

Figure 4:
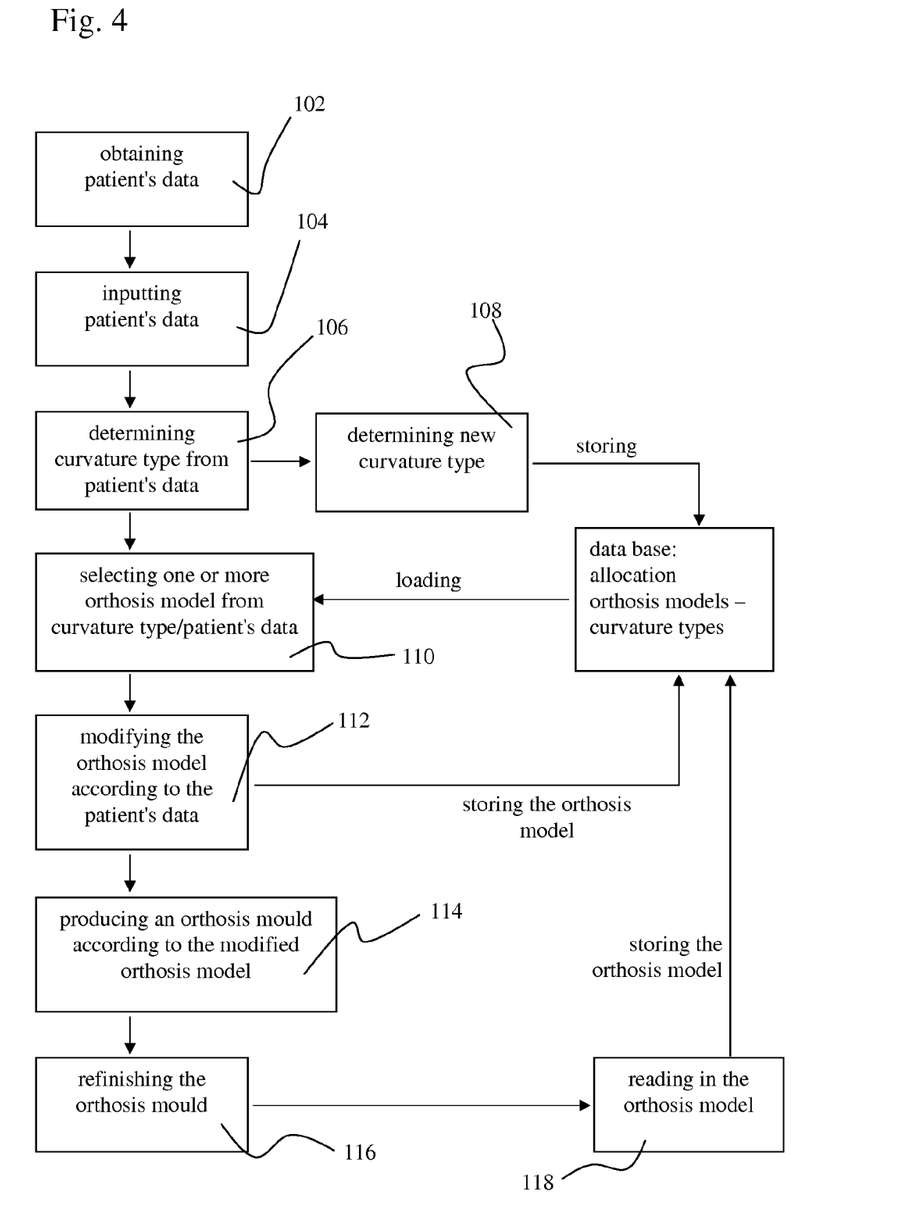
FIG. 4 shows a flow chart of an embodiment of the method according to the invention.

FIG. 4 shows a flow chart of the method according to the invention. In step 102, patient's data are obtained, e.g. radiographs are made. In 104 said data are inputted. In 106 the curvature type is determined from the patient's data, for instance, mainly from the radiograph. If the curvature type is detected to be new, the new curvature type can be determined and stored in the data base in step 108. An orthosis model is selected from the curvature type and/or the patient's data in 110, and the selected model is loaded from the data base. In step 112 said model is modified in correspondence with the individual patient's data. In this case, it may also be stored in the data base, if necessary, if the circumference justifies the modification, for instance. The orthosis mould is now produced according to the modified model, 114. The manual refinishing may take place in step 116. The processed orthosis mould is then read in, 118, so that the corresponding model can be stored in the data base. Thus, the production for the patient in question is concluded.

The orthosis mould to be produced is based on orthoses models affecting a desired deformation of the patient's spine. It is conceivable that a first orthosis is applied to correct the original curvature, while another orthosis is produced after a certain wearing period so as to additionally correct the already provisionally corrected spine. The present method can be applied to both process steps.

Figure 5:
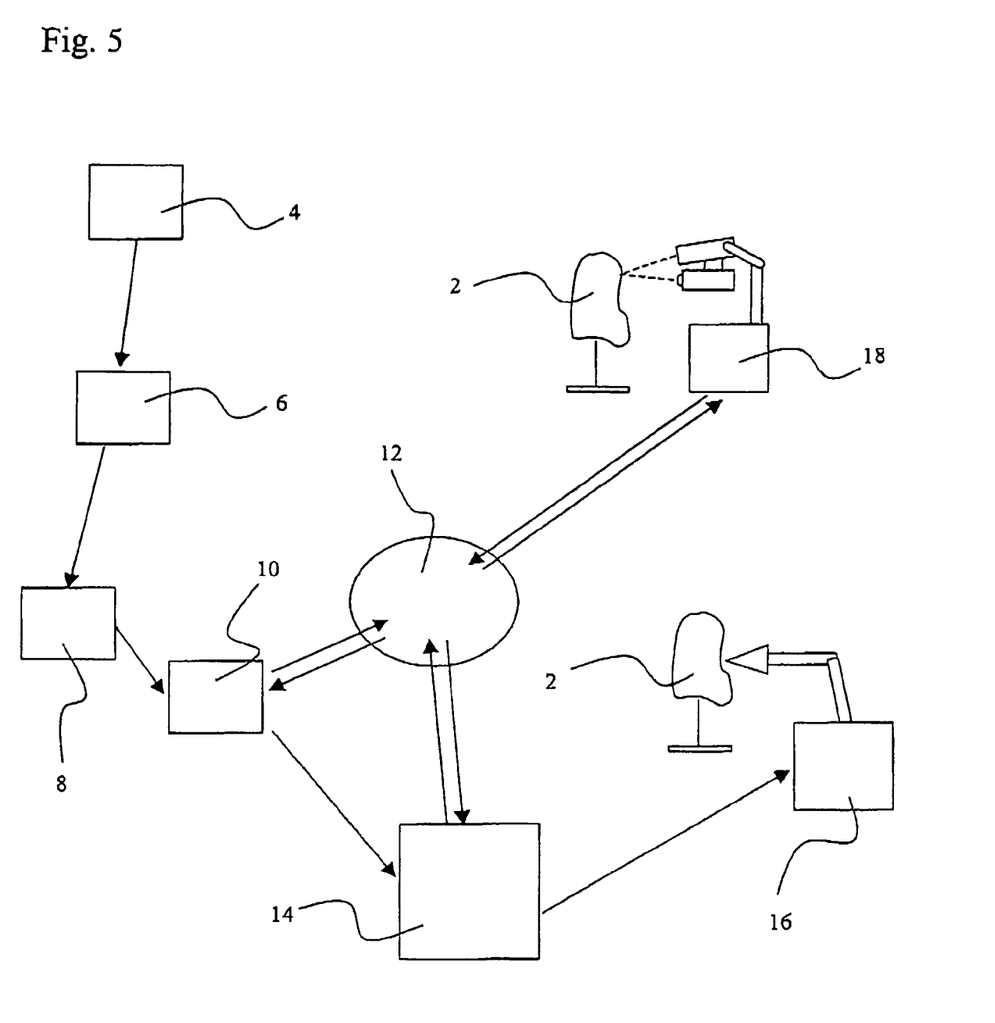
FIG. 5 shows an embodiment of the device according to the invention.

FIG. 5 shows a device according to the present invention. The device comprises a data obtainment device 4 for obtaining the data of a patient. The data are inputted in a data input device 6. A curvature determination device 8 is designed to determine the abstract curvature type from the patient's data. The curvature type is transferred to an orthosis model selection device 10 which selects, with access to a data base 12, one or more orthoses models suited for the type of curvature and, if necessary, subsequently selects one from the plurality according to the patient's data. In a data processing system 14 the selected model can be adapted to the patients data, i.e. be scaled to the body height, for instance. The data processing system 14 can fulfill additional tasks, such as the storing of modified models as new orthoses models, or the determination and also the storing of a newly detected curvature type in the data base. Also, allocations in the data base between curvature type and orthoses models may be adapted/modified or generated anew, if necessary. Final orthoses moulds according to the selected models are then produced by a shaping device 16, e.g. a CNC-cutter. In the case where such moulds have to be refinished, they may again be stored in the data base by means of a reading-in device 18, e.g. a laser scanner, so as to be available in the future.

Figure 6:
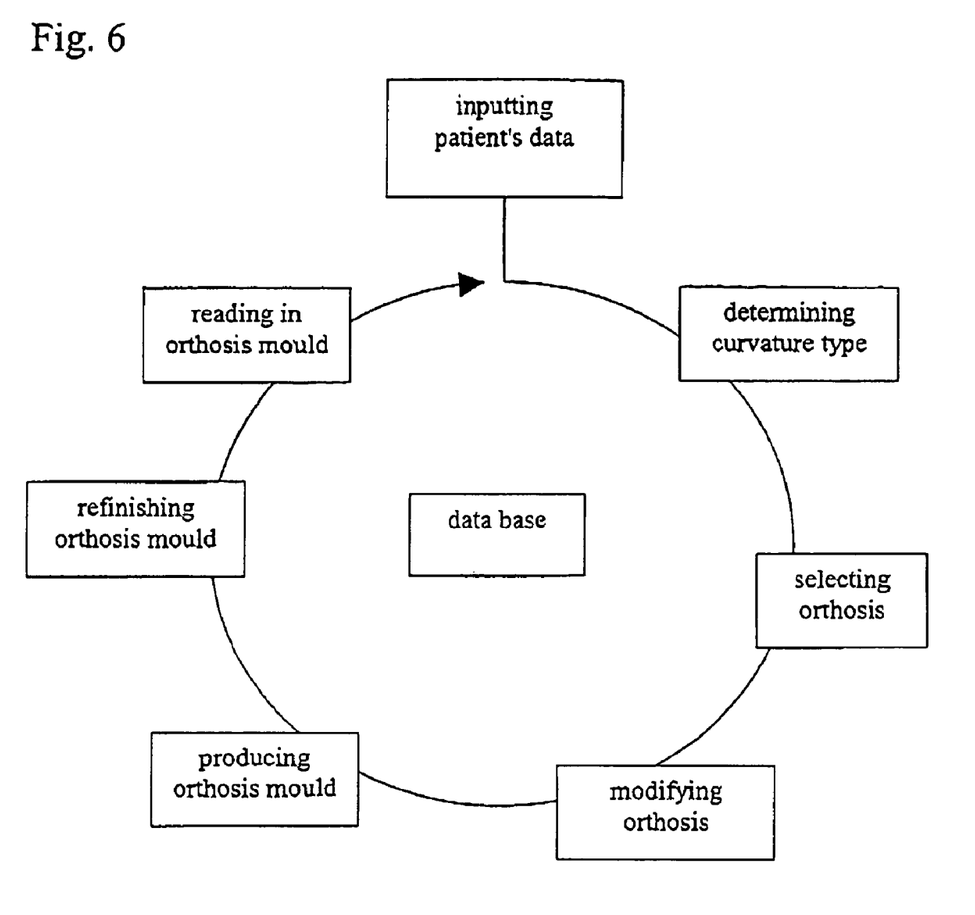
FIG. 6 shows a cyclic diagram of an embodiment of the method according to the invention.

FIG. 6 shows a diagram of a cycle destined to proceed in accordance with the method of the present invention. Patients' data are inputted, whereupon the curvature type is determined. An appropriate orthosis model is then selected. According to the patient's data this model is then adapted, i.e. modified, to the individual wearer. The orthosis or, respectively, the orthosis mould can then be produced. At this stage, the adapted orthosis could be stored in the data base in which the curvature types and orthoses are stored. Manual refinishing may be required, e.g. during the fitting. In this case, the processed orthosis mould has to be read in first, before it can likewise be stored in the data base in allocation to the corresponding curvature type. In a cycle system of this type new orthoses moulds for future patients are made available. Thus, the system is self-adapting, i.e. selections for future patients can be made from a broader data base, and more orthoses models are available for a finer selection. Not shown in this diagram is the entry of a new curvature type if the same is detected. Such a new curvature type may, however, flow into the data base analogously as to be available for future selections.

The invention claimed is:

1. A computer implemented method for producing an orthosis model for a spine of a patient comprising the steps of:
   inputting patient data corresponding to a curvature of the patient's spine with a data input device;
   determining a curvature type of the patient's spine from a predefined number of curvature types stored in a data base with a curvature determination device on the basis of the patient's data wherein the curvature type is defined by a number of points of deflection of an abstract spine and one or more directions of curvature of the abstract spine; and
   selecting at least one orthosis model from a predefined number of orthosis models with a model selection device on the basis of the determined curvature type.

2. The computer implemented method according to claim 1, wherein said inputting step is further defined as:
   inputting at least one of radiographs, photographs of a back of the patient, status body dimensions o the patient, dynamic body dimensions of the patient, and age of the patient to the data input device.

3. The compute implemented method according to claim 1 wherein said selecting step is further defined as:
   selecting a plurality of orthosis models in dependence on the patient's data.

4. The computer implemented method according to claim 1 further comprising the step of:
   obtaining the patients data corresponding to factors independent of the curvature of the spine.

5. The computer implemented method according to claim 1 further comprising the step of: modifying the selected orthosis model in response to patient's data corresponding to factors independent of the curvature of the spine.

6. The computer implemented method according to claim 5 further comprising the steps of:
   adding the modified orthosis model to the predefined number of orthosis models.

7. The computer implemented method according to claim 6 further comprising the step of:
   producing an orthosis mould according to one of the selected and the modified orthosis model.

8. The computer implemented method according to claim 7 further comprising the step of:
   refinishing the produced orthosis mould.

9. The computer implemented method according to claim 7 further comprising the steps of:
   reading in the refinished orthosis mould with a reading-in device as an orthosis model; and
   adding the orthosis model read-in during said reading in step to the predefined number of orthosis models.

10. The computer implemented method according to claim 1 wherein said determining step includes the steps of;
    assigning a new curvature type based on the patient's data; and
    adding the new curvature type to the predefined number of curvature types in the data base.

11. The computer implemented device for producing an orthosis model for a spine of a patient, comprising:
    a data input device for inputting a patient's data corresponding to a curvature of the patient's spine;
    a data base containing a number of curvature types and a number of orthosis models wherein each curvature type is defined by a number of points of deflection of an abstract spine and one or more directions of curvature of the abstract spine and wherein at least one orthosis model is associated with each curvature type;
    a curvature determination device to determine a curvature type from among said number of curvature types in said data base on the basis of the patient's data corresponding to the curvature of the patient's spine; and
    an orthosis model selection device to select at least one orthosis model from said data base on the basis of the determined curvature type.

12. The computer implemented device according to claim 11, wherein said data base is farther defined as correlating said curvature types with said orthosis models with one of one-valued relationships and many-valued relationships, and wherein said orthosis model selection device is further defined as being operable to select at least one orthosis model on the basis of said relationships.

13. The computer implemented device according to claim 12, wherein said orthosis model selection device selects at least two orthosis models on the basis of said relationships, and wherein said orthosis model selection device selects one orthosis model from said at least two orthosis models in dependence on the patient's data corresponding to a curvature of the patient's spine.

14. The computer implemented device according to claim 13 further comprising:
    a device for obtaining patient's data corresponding to factors independent of the curvature of the spine, wherein the device inputs the obtained patient's data corresponding to factors independent of the curvature of the spine into said data input device.

15. The computer implemented device according to claim 14, further comprising:
    a data processing system operable to modify the selected orthosis model according to the patient's data corresponding to factors independent of the curvature of the spine.

16. The computer implemented device according to claim 15 wherein said data processing system adds the modified orthosis model to the number of orthosis models in said data base.

17. The computer implemented device according to claim 16 wherein said data processing system modifies the curvature types and orthosis models in said data base.

18. The computer implemented device according to claim 17, further comprising:
    a shaping device for producing an orthosis mould according to one of the selected and modified orthosis model.

19. The device according to claim 18, further comprising:
    a reading-in device for reading in an orthosis mould and adding an orthosis model according to the read-in orthosis mould to the number of orthosis models in the data base.

20. The computer implemented device according to claim 19, wherein said data processing system determines a new curvature type from the patient's data corresponding to a curvature of the patient's spine and adds the new curvature type to the number of curvature types in said data base.

* * * * *

UNITED STATES PATENT AND TRADEMARK OFFICE
CERTIFICATE OF CORRECTION

PATENT NO.          : 7,283,883 B2                                          Page 1 of 1
APPLICATION NO.     : 10/802315
DATED               : October 16, 2007
INVENTOR(S)         : Jenny Voit and Dino Gallo It is certified that error appears in the above-identified patent and that said Letters Patent is hereby corrected as shown below:

| Column | Line | |
|--------|------|---|
| 9 | 37 | Replace "obtaining the patients" with -- obtaining patients -- |
| 10 | 17 | Replace "farther" with -- further -- |

Signed and Sealed this

Eighteenth Day of December, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,283,883 B2 | Page 1 of 1 |
| APPLICATION NO. | : 10/802315 | |
| DATED | : October 16, 2007 | |
| INVENTOR(S) | : Jenny Voit and Dino Gallo | |

It is certified that error appears in the above-identified patent and that said Letters Patent is hereby corrected as shown below:

On the Title Page
Item (73) Assignee: "Ortho Solutions" should be "Ortholutions OHG"

Signed and Sealed this
Seventeenth Day of May, 2011

David J. Kappos
*Director of the United States Patent and Trademark Office*